US006051043A

United States Patent [19]
Kitten

[11] Patent Number: 6,051,043
[45] Date of Patent: Apr. 18, 2000

[54] SUGAR MOBILIZING AND INSECT COMBATTING FERTILIZER COMPOSITION AND USE

[76] Inventor: Jerry Kitten, Rte. 2 Box 6, Slaton, Tex. 79364

[21] Appl. No.: 08/149,766

[22] Filed: Nov. 10, 1993

Related U.S. Application Data

[63] Continuation-in-part of application No. 08/000,224, Jan. 4, 1993, abandoned.
[51] Int. Cl.[7] .................................................. C05F 11/02
[52] U.S. Cl. ............................. 71/24; 71/11; 71/23; 71/27
[58] Field of Search ................................. 71/1, 11, 23, 24, 71/27, DIG. 2

[56] References Cited

U.S. PATENT DOCUMENTS 4,652,294  3/1987  Arnold ........................................ 71/28

FOREIGN PATENT DOCUMENTS 744379  6/1970  Belgium .
2314905  2/1977  France ........................................ 71/24

OTHER PUBLICATIONS

Visser, "Effects of Humic Substances on Plant Growth", REDA, Rome 1986, pp. 89–135.

Chen and Aviad, "Effects of Humic Substances on Plant Growth", Humic Substances in Soil and Crop Sciences, Selected Readings, 1990, pp. 161–186.

Consumer Product Data Sheets for Charge™, Foli–Zyme™ and Sett™ (no date available).

*Primary Examiner*—Tom Dunn
*Attorney, Agent, or Firm*—Jacobson, Price, Holman & Stern, PLLC

[57] ABSTRACT

Sprayable aqueous fertilizer compositions comprising humic acid in combination with nitrogen, phosphorus, calcium and boron, when applied to sugar-containing plant leaves, achieves a dual purpose of significantly altering the sugar-content of such leaves and eliminating infestation of such leaves by sugar-eating, slow-moving, soft-bodied insects.

15 Claims, No Drawings

SUGAR MOBILIZING AND INSECT COMBATTING FERTILIZER COMPOSITION AND USE

RELATED APPLICATION

This application is a continuation-in-part application of application Ser. No. 08/000,224, filed on Jan. 4, 1993 now abandoned.

FIELD OF THE INVENTION

Humic-acid-containing aqueous fertilizer compositions, sprayed on plant leaves which have a sugar concentration which attracts and supports certain insects, significantly alters the sugar concentration in the plant leaves, which discourages or eliminates infestation of the plants by such insects.

BACKGROUND

The essential fertilizer components, humic acid, nitrogen, phosphorus, calcium and boron, have all been used in fertilizer compositions. Some of these components are shown, e.g., by Hoover (U.S. Pat. No. 4,069,034). A single company, Stoller, Inc., manufactures or provides three products, Charge™, Sett™, and Foli-Zyme™, which are regarded individually as fertilizer components. Charge™ is characterized as a humic acid concentrate manufactured by a patented process which extracts humic acid directly from undecomposed peat naturally without use of caustic chemical processes. The active ingredients are stated to be humic and related acids (15%).

Sett™ is designed to be sprayed on plant foliage to reduce localized ethylene production within the plant. It is also supposed to guard against calcium replacement in cell walls and to increase fruit, boll, pod, or bud set. It is a foliar nutritional for reduced fruit shedding which comprises 8% calcium and 1% boron, derived from calcium sucrose and sodium borate.

Foli-Zyme™ is stated to be a fluid nutrient compound designed to prevent nutrient deficiencies in plants, a valuable supplement to soil-applied nutrients and particularly beneficial under conditions where soil nutrients are not readily available. It has a pH of from 1.5 to 2.5 and has a minimum guaranteed analysis of 15% total nitrogen, 2% available phosphoric acid ($P_2O_5$) and 3% calcium; these components are stated to be derived from urea-phosphate, calcium monocarbamide monohydrogen chloride and N-hib™ calcium.

SUMMARY OF THE INVENTION

An aqueous and sprayable fertilizer composition comprising humic acid in combination with nitrogen, phosphorus, calcium and boron, when sprayed on plant leaves, which have a sugar concentration which attracts and supports slow-moving, soft-bodied insects, aids in growth and health of the plant and significantly alters the sugar concentration in the plant leaves.

An object of the invention is to provide a fertilizer composition which is capable of altering the sugar concentration in sugar-containing plant leaves when sprayed on such leaves. A further object of the invention is to provide a composition for combatting infestation on sugar-containing plant leaves of sugar-eating, slow-moving, soft-bodied insects by applying a liquid fertilizer to such leaves. A still further object of the invention is to move sugar from sugar-containing plant leaves to fruit of the plant by applying an aqueous fertilizer composition to the plant leaves.

DETAILS

Ordinary fertilizers contain, e.g., nitrogen, phosphorus, potassium, calcium, and trace elements, such as boron. Combining humic acid with nitrogen, phosphorus, calcium and boron in suitable proportions in an aqueous sprayable fertilizer composition provides a formulation which, when sprayed on plant leaves which have a sugar concentration which attracts and supports slow-moving, soft-bodied insects, not only aids in the growth and health of the plant but also significantly alters the sugar concentration in the plant leaves. This discourages infestation by the sugar-eating, slow-moving, soft-bodied insects, such as aphids, which feed on such leaves. Applying the aqueous fertilizer composition to the leaves eliminates the noted detrimental insects by removing or adequately altering that which attracts such insects.

The aqueous fertilizer compositions advantageously contain (by volume) from about 4.2 to about 7.8 (preferably about 6) parts of nitrogen, from 0.56 to 1.04 (preferably about 0.8) parts of phosphoric anhydride ($P_2O_5$), from 3.08 to 5.72 (preferably about 4.4) parts of calcium, from 0.28 to 0.52 (preferably about 0.4) part of boron, and from 2.1 to 3.9 (preferably about 3) parts of humic acid. These essential components are advantageously mixed with a base of inert ingredients, although other active fertilizer components can also be incorporated in the aqueous fertilizer compositions. The essential elements are combined in liquid form in, e.g., stainless steel vats or other suitable containers which do not disintegrate when exposed to humic or phosphoric acids.

The noted essential components (humic acid, nitrogen, phosphorus, calcium and boron) are mixed with water to produce a sprayable composition which is applied by ground or air spraying, as is common with liquid fertilizers currently used.

Humic acid is actually a generic term. For this disclosure that term is limited to the humic and related acids of the type referred to in the characterization of active ingredients in Charge™. The humic and related acids are, e.g., those obtained according to the disclosure of U.S. Pat. No. 4,459,149. This humic acid is directly extracted from undecomposed peat naturally and without use of caustic chemical processes. The humic acid is limited to that which, in combination with suitable proportions of nitrogen, phosphorus, calcium and boron, is capable of significantly altering the sugar concentration of sugar-containing plant leaves on which it is applied.

The term "significantly", as used in connection with altering the sugar concentration in sugar-containing plant leaves, refers to a degree of change in concentration sufficient to discourage the sugar-eating, slow-moving, soft-bodied insects sufficiently so that they will stop foraging on the involved plant leaves. The change in concentration is normally a decrease in concentration, but is, occasionally, an increase in sugar concentration.

When applied to plant leaves which have a sugar concentration which attracts and supports sugar-eating, slow-moving, soft-bodied insects, the aqueous fertilizer compositions alter significantly the sugar concentration in the plant leaves. By so doing, the composition is effective in combatting the sugar-eating, slow-moving, soft-bodied insects, such as aphids, whitefly larvae and spider mites, which feed on the sugar content found in the leaves of many plants. Plants, which are doing poorly, produce more sugars than they are able to process. As a result, the excess sugar attracts aphids and other soft-bodied, slow-moving insects. Although ordinary fertilizers can help strengthen the plants so that the excess sugar level is decreased, that process is slow and normally unsuccessful before the leaves are already infested with or destroyed by the insects. The humic acid in the subject compositions mobilizes the sugar; the other critical ingredients (nitrogen, phosphorus, calcium and boron) act as a catalyst to alter the sugar concentration in the leaves. For numerous plants, the sugar is moved from the leaves to the fruit. Without an appropriate sugar concentration in the leaves, the insects no longer have an interest in the plant. Consequently, the sugar-eating, slow-moving, soft-bodied insects abandon the plant to look elsewhere for food. However, because they are slow moving, they often starve to death before finding food. Being rid of the insects, the plant then has time to regain its health and break down the normally-produced sugars. The composition works to rid the plant of insects and to strengthen the plant while also saving beneficial insects. The beneficial insects help to control any remaining aphids, as well as other fruit-eating insects.

Although suitable aqueous compositions can be prepared by virtually any established means of combining the required components, suitable compositions are prepared by combining two two parts parts by volume of Foli-Zyme™ with two parts by volume of Sett™ and one part by volume of Charge™. The resulting blend is suitably diluted with various amounts of water just prior to foliar application. The amount of water added depends on the size and type of crop to be treated. Also, other fertilizer components can be incorporated in the formulation, as desired. Other trace elements improve the obtained results by furnishing catalysts suitable for forming plant enzymes.

The stated essential components other than humic acid, i.e. nitrogen, phosphorus, calcium and boron, are optionally in any form commonly used in fertilizer compositions. The nitrogen is preferably organic nitrogen, and the phosphorus is preferably in the form of phosphoric anhydride, sometimes referred to as phosphoric acid.

Although the actual parts by weight or parts by volume of each of the essential components may vary to some degree, the approximate relationship between the noted essential components should be six parts by volume of nitrogen, 0.8 part by volume of phosphoric anhydride, 4.4 parts by volume of calcium and 0.4 part by volume of boron for each 3 parts by volume of humic acid. The actual parts by weight of the respective essential ingredients can vary from 4.15 to 7.71 (preferably about 5.93) parts of nitrogen, from 0.55 to 1.03 (preferably about 0.79) parts of phosphoric anhydride, from 3.32 to 6.16 (preferably about 4.74) parts of calcium, from 0.31 to 0.58 (preferably about 0.44) part of boron and from 1.69 to 3.14 (preferably about 2.41) parts of humic acid.

The humic acid acts in consort with the other essential components to alter the sugar concentration in sugar-containing leaves of plants sufficiently to reduce or eliminate infestation of such plants by the noted sugar-eating insects. The aqueous fertilizer compositions are thus capable of altering the sugar concentration in plant leaves to which the composition is applied. It is capable of assisting the transport of such sugar from the leaves to the fruit of such plants. It is also capable of exterminating sugar-eating insects or at least removing them from sugar-containing plant leaves.

The invention and its advantages are readily understood from the preceding description. Various changes may be made in the compositions and processes without departing from the spirit and scope of the invention or sacrificing its material advantages. The processes and compositions hereinbefore described are merely illustrative of preferred embodiments of the invention.

I claim:

1. A method for combatting sugar-eating, slow-moving, soft-bodied insects which thrive on sugar-containing plant leaves, which comprises spraying on such leaves, infested with the insects, an effective amount of a fertilizer composition comprising a combination of humic acid with nitrogen, phosphorus, calcium and boron, each of which is present therein in an effective amount, and the humic acid is of a type which is suitable, in the presence of an effective amount of nitrogen, phosphorus, calcium and boron, to alter significantly the sugar concentration in the plant leaves on which said fertilizer composition is sprayed.

2. A method of claim 1, in the fertilizer composition of which the approximate volumetric relationship among nitrogen, calcium, humic acid, phosphoric anhydride and boron is 6 parts of nitrogen, 4 parts of calcium, 3 parts of humic acid, 0.8 part of phosphoric anhydride and a trace of boron.

3. A method of claim 1 wherein the humic acid is a noncaustic and direct extract of undecomposed peat.

4. A method of claim 1 in which the composition comprises, by volume, from 4.2 to 7.8 parts of nitrogen, from 0.56 to 1.04 parts of phosphoric anhydride ($P_2O_5$), from 3.08 to 5.72 parts of calcium, from 0.28 to 0.52 part of boron and from 2.1 to 3.9 parts of humic acid.

5. A method of claim 4 in which the composition comprises, by volume, approximately 6 parts of nitrogen, approximately 0.8 part of phosphoric anhydride ($P_2O_5$), approximately 4.4 parts of calcium, and approximately 0.4 part of boron for each 3 parts of humic acid.

6. A method of claim 5 wherein the nitrogen is derived from urea or a salt thereof, the calcium is derived from calcium sucrose or a calcium carbamide, and the boron is derived from sodium borate.

7. A method of claim 1 in which the composition comprises 2 parts by volume of each of Foli-zyme™ and Sett™ for each part by volume of Charge™.

8. A method of claim 1 wherein the sole essential fertilizer components are humic acid, nitrogen, phosphorus, calcium and boron.

9. A method of claim 1, in the fertilizer composition of which from 4.2 to 7.8 parts by volume consist of nitrogen, from 0.56 to 1.04 parts by volume consist of phosphoric anhydride ($P_2O_5$), from 3.08 to 5.72 parts by volume consist of calcium, from 0.28 to 0.52 part by volume consists of boron and from 2.1 to 3.9 parts by volume consist of humic acid.

10. A method of claim 1, in the fertilizer composition of which from 4.15 to 7.71 parts by weight consist of nitrogen, from 0.55 to 1.03 parts by weight consist of phosphoric anhydride ($P_2O_5$), from 3.32 to 6.16 parts by weight consist of calcium, from 0.31 to 0.58 part by weight consists of boron and from 1.69 to 3.14 parts by weight consist of humic acid.

11. A method of claim 1, the fertilizer composition of which comprises, by weight, about 1.96 parts of calcium, about 0.18 part of boron, about 2.46 parts of nitrogen and about 0.33 part of $P_2O_5$ per part of humic acid.

12. A method of claim 1 wherein the insects are aphids.

13. A method of combating sugar-eating, slow-moving, soft-bodied insects which thrive on and infest sugar-containing plant leaves, which comprises sufficiently altering sugar concentration in such leaves, when infested with the insects to discourage such insects.

14. A method of claim 13 which comprises reducing the sugar content of such leaves to a level below that required by the insects.

15. A method of claim 14 wherein the insects are aphids.

* * * * *